Figure 1:
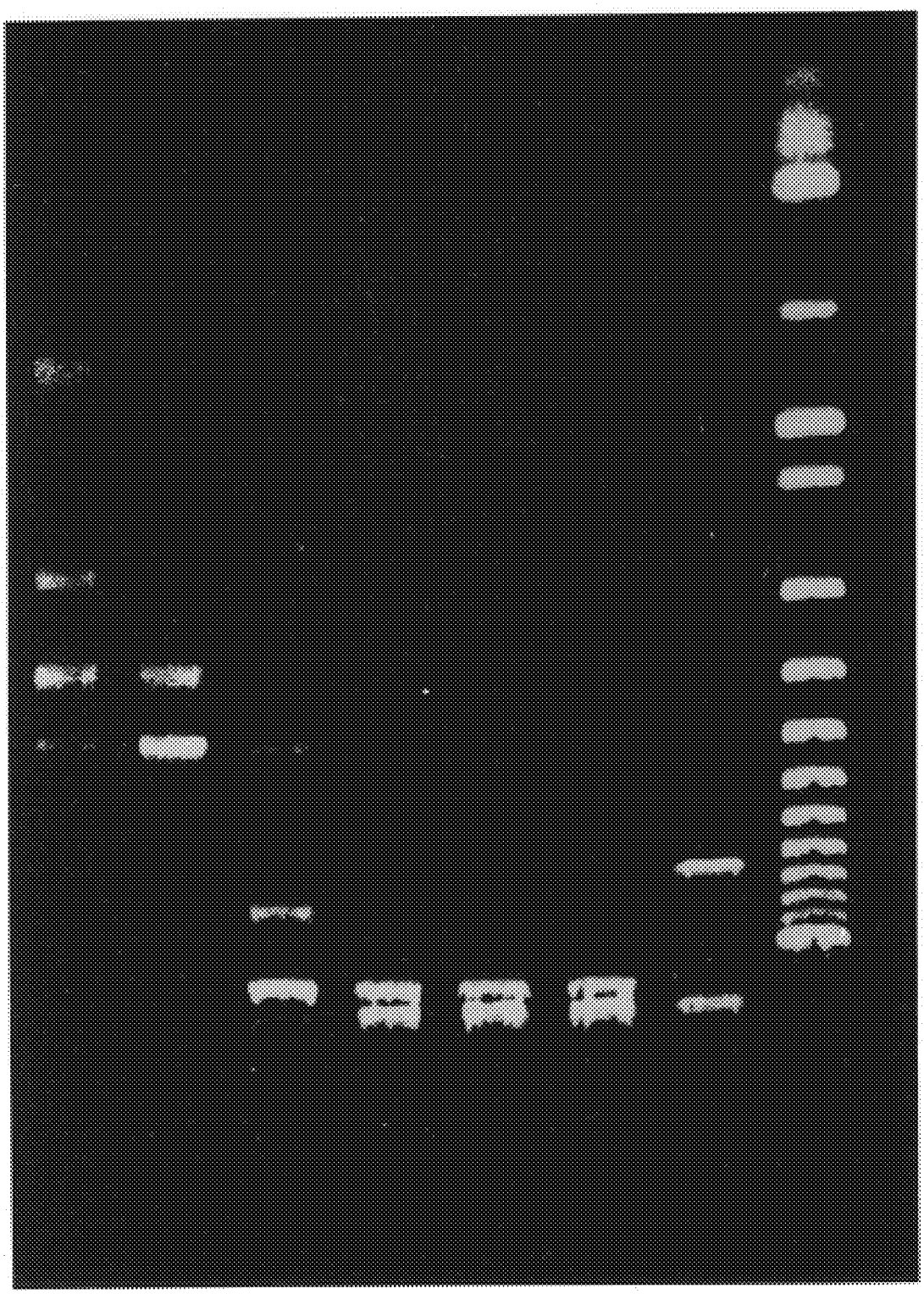

United States Patent [19]

Schwemler et al.

[11] Patent Number: 5,955,571
[45] Date of Patent: *Sep. 21, 1999

[54] NUCLEIC ACID-BINDING OLIGOMERS FOR THERAPY AND DIAGNOSIS

[75] Inventors: Christoph Schwemler, Leichlingen; Thorsten Pötter, Köln; Burkhard Mielke, Leverkusen; Eckhard Schwenner, Wuppertal; Axel Kretschmer, Bergisch Gladbach; Udo Stropp, Haan; Winfried Kosch, Köln; Hansjörg Dürr, Burscheid, all of Germany

[73] Assignee: Bayer Aktiengesellschaft, Leverkusen, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/509,913

[22] Filed: Aug. 1, 1995

[30] Foreign Application Priority Data

Aug. 8, 1994 [DE] Germany .............................. 44 27 980

[51] Int. Cl.$^6$ ...................................................... C07K 5/00
[52] U.S. Cl. .......................... 530/300; 530/350; 436/501; 435/6; 935/77; 935/78
[58] Field of Search ........................ 435/6, 810; 436/501; 530/300, 350; 536/23.1, 24.1, 24.3–24.33; 935/77, 78

[56] References Cited

FOREIGN PATENT DOCUMENTS

| 4331012 | 3/1995 | Germany . |
|---|---|---|
| 8605518 | 9/1986 | WIPO . |
| 9218518 | 10/1992 | WIPO . |
| 9220702 | 11/1992 | WIPO . |
| 9220703 | 11/1992 | WIPO . |
| 9304701 | 3/1993 | WIPO . |
| 9312129 | 6/1993 | WIPO . |
| 9425477 | 11/1994 | WIPO . |

OTHER PUBLICATIONS

P.E. Nielsen, et al., Bioconjugate Chem., vol. 5, No. 1, pp. 3–7, (1994).
S. Agrawal, Tibtech, vol. 10, pp. 152–158, (1992).
W. James, Antiviral Chemistry & Chemotherapy, vol. 2, No. 4, pp. 191–214, (1991).
B. Calabretta, Cancer Research, vol. 51, pp. 4505–4510, (1991).
C. Helène, Anti–Cancer Drug Design, vol. 6, pp. 569–584, (1991).
E. Uhlmann, et al., Chemical Reviews, vol. 90, No. 4, pp. 544–584, (1990).
C. Clusel, et al., Nucleic Acids Research, vol. 21, No. 15, pp. 3405–3411, (1993).
J. Pitha, et al., The Journal of Organic Chemistry, vol. 88, No. 4, pp. 1341–1344, (1968).
J. Pitha, Advances in Polymer Science, pp. 1–16, (1983).
H. Wang, et al., Tetrahedron Letters, vol. 32, No. 50, pp. 7385–7388, (1991).

(List continued on next page.)

Primary Examiner—Ardin H. Marschel
Attorney, Agent, or Firm—Sprung Kramer Schaefer & Briscoe

[57] ABSTRACT

The present invention relates to compounds of the general formula (I), in which the radicals have the meaning given in the description, to processes for their preparation and to their use as medicaments.

3 Claims, 2 Drawing Sheets

OTHER PUBLICATIONS

P. Garner, et al., Tetrahedron Letters, vol. 34, No. 8, pp. 1275–1278, (1993).

S–B. Huang, et al., J. Org. Chem., vol. 56, No. 21, pp. 6007–6018, (1991).

G. Barany, et al., Int. J. Peptide Protein Res., vol. 30, pp. 705–739, (1987).

D.J. Rose, Anal. Chem., vol. 65, No. 24, pp. 3545–3549, (1993).

A.E. Barron, et al., Journal of Chromatography A, vol. 652, pp. 3–16, (1993).

G.B. Fields, et al., Int. J. Peptide Protein Res., vol. 35, pp. 161–214, (1990).

R.B. Merrifield, Synthesis of a Tetrapeptide, vol. 85, pp. 2149–2154, (1963).

SEQUENCE LISTING (1) GENERAL INFORMATION:

(iii) NUMBER OF SEQUENCES:   6

(2) INFORMATION FOR SEQ ID NO: 1:

(i) SEQUENCE CHARACTERISTICS:
        (A) LENGTH: 12 nucleotides
        (B) TYPE: nucleic acid
        (C) STRANDEDNESS:  single
        (D) TOPOLOGY: linear (xi) SEQUENCE DESCRIPTION: SEQ ID NO: 1:

TTTTTTTTTT TT                                              12

(2) INFORMATION FOR SEQ ID NO: 2:

(i) SEQUENCE CHARACTERISTICS:
        (A) LENGTH: 12 nucleotides
        (B) TYPE: nucleic acid
        (C) STRANDEDNESS:  single
        (D) TOPOLOGY: linear (xi) SEQUENCE DESCRIPTION: SEQ ID NO: 2:

TTTTTTTTTT TT                                              12

(2) INFORMATION FOR SEQ ID NO: 3:

(i) SEQUENCE CHARACTERISTICS:
        (A) LENGTH: 12 nucleotides
        (B) TYPE: nucleic acid
        (C) STRANDEDNESS:  single
        (D) TOPOLOGY: linear (xi) SEQUENCE DESCRIPTION: SEQ ID NO: 3:

TTTTTTTTTT TT                                              12

(2) INFORMATION FOR SEQ ID NO: 4:

(i) SEQUENCE CHARACTERISTICS:
        (A) LENGTH: 12 nucleotides
        (B) TYPE: nucleic acid
        (C) STRANDEDNESS:  single
        (D) TOPOLOGY: linear (xi) SEQUENCE DESCRIPTION: SEQ ID NO: 4:

TTTTTTTTTT TT                                                  12

(2) INFORMATION FOR SEQ ID NO: 5:

(i) SEQUENCE CHARACTERISTICS:
        (A) LENGTH: 12 nucleotides
        (B) TYPE: nucleic acid
        (C) STRANDEDNESS: single
        (D) TOPOLOGY: linear (xi) SEQUENCE DESCRIPTION: SEQ ID NO: 5:

TTTTTTTTTT TT                                                  12

(2) INFORMATION FOR SEQ ID NO: 6:

(i) SEQUENCE CHARACTERISTICS:
        (A) LENGTH: 12 nucleotides
        (B) TYPE: nucleic acid
        (C) STRANDEDNESS: single
        (D) TOPOLOGY: linear (xi) SEQUENCE DESCRIPTION: SEQ ID NO: 6:

AAAAAAAAAA AA                                                  12

NUCLEIC ACID-BINDING OLIGOMERS FOR THERAPY AND DIAGNOSIS

The specific switching-off of gene expression by complementary nucleic acids, so-called antisense oligonucleotides, represents a new approach to therapy. Possible applications extend from the treatment of viral infections through to cancer therapy (S. Agrawal, Tibtech 10, 152 (1992); W. James, Antiviral Chemistry & Chemotherapy 2, 191 (1991); B. Calabretta, Cancer Research 51, 4504 (1991)). Gene expression is controlled at the DNA and RNA level and is achieved even using unmodified oligonucleotides (C. Helene, Anti-Cancer Drug Design 6, 569 (1991); E. Uhlmann, A. Peymann, Chemical Reviews 90, (1990)). However, the latter are not suitable for therapeutic applications because of their lack of stability towards enzymes and because they are not taken up to a sufficient extent by cellular systems. Therapeutic applications require chemically modified antisense oligonucleotides.

Apart from the antisense strategy, the sense strategy can also be used to inhibit gene expression. In this case, the sense oligonucleotides compete specifically with DNA binding proteins such as transcription factors (M. Blumengeld, Nucleic Acids Research 21, 3405 (1993)).

Oligonucleotides having a modified internucleotide phosphate or a phosphate-free internucleotide linkage have been investigated systematically in many studies; however, their synthesis was found to be very elaborate and their reported therapeutic effects were not adequate (E. Uhlmann, A. Peyman, Chemical Reviews 90, 543 (1990)).

An alternative to modifying or substituting the phosphate group in nucleic acids is completely to replace ribose and phosphate by other backbones. This concept was first realized by Pitha et al., who replaced ribose phosphate by poly-N-vinyl derivatives, resulting in so-called "plastic DNA" (J. Pitha, P.O.P. Ts'O, J. Org. Chem. 33, 1341 (1968); J. Pitha, J. Adv. Polym. Sci. 50, 1 (1983)). However, this does not permit the specific construction of defined sequences.

Synthesis of defined sequences is achieved if, for example, a polyamide backbone, which is constructed stepwise in analogy with conventional peptide synthesis (M. Bodanszky, Principles of Peptide Synthesis, Springer, Berlin 1984), is used instead of sugar phosphate. This concept has been realized in different ways by different research groups (J. E. Summerton et al., WO 86/05518; R. S. Varma et al., WO 92/18518; O. Buchardt et al., WO 92/20702; H. Wang, D. D. Weller, Tetrahedron Letters 32, 7385 (1991); P. Garner, J. U. Yoo, Tetrahedron Letters 34; 1275 (1993); S.-B. Huang, J. S. Nelson and D. D. Weller; J. Org. Chem. 56; 6007 (1991)).

Polyamide nucleic acids are also suitable for use in diagnostic and molecular biological applications (Buchardt et al., WO 92/20703 and Glaxo, WO 93/12129).

During the processing of this type of structure, success was achieved in synthesizing novel N-branched oligomeric nucleic acids. The latter were found to bind surprisingly well to DNA and RNA. The substances are suitable for controlling gene expression and exhibit antiviral properties. Furthermore, substances of this nature can be used in diagnostics and molecular biology for isolating, identifying and quantifying nucleic acids.

The invention relates to compounds of the general formula (I),

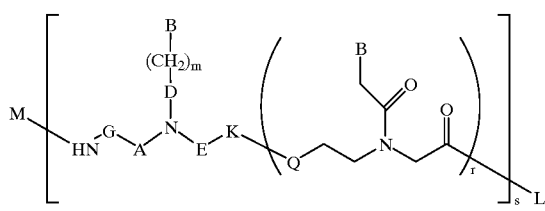

in which

A represents —$(CH_2)_n$— or —CO—,

B represents all natural or unnatural nucleotide bases, such as, for example, thymine, uracil, cytosine, adenine, guanine or hypoxanthine, or derivatives derived therefrom by means of chemical modification, or halogenated precursors thereof, which are optionally substituted on the amino groups by protective groups such as acetyl, trifluoroacetyl, trichloroacetyl, benzoyl, phenylacetyl, benzyloxycarbonyl, tert-butyloxycarbonyl, allyloxycarbonyl, (9-fluorenyl) methoxycarbonyl or other protective groups which are customary in peptide and nucleic acid chemistry, or which have free amino groups, D represents —$(CO)_p$—, E and G, independently of each other, represent —CHR—, where R represents H or a residue of a natural or unnatural amino acid, for example from glycine, alanine, valine, leucine, isoleucine, serine, threonine, cysteine, methionine, phenylalanine, tyrosine, histidine, tryptophan, lysine, ornithine, asparagine, aspartic acid, glutamine, glutamic acid, arginine, proline, hydroxyproline, sarcosine, dehydroamino acids, such as, for example, dehydroalanine or dehydro-α-aminobutyric acid, or other unnatural amino acids, such as phenylglycine, 4-nitrophenylalanine, 3-nitrophenylalanine, 2-nitrophenylalanine, 2-, 3- or 4-aminophenylalanine, 3,4-dichlorophenylalanine, 4-iodophenylalanine, 4-methoxyphenylalanine, 1-triazolylalanine, 2-pyridylalanine, 3-pyridylalanine, 4-pyridylalanine, 1-naphthylalanine or 2-naphthylalanine, optionally having protective groups, in their D or L form, or, where appropriate, E and G are linked to each other by way of a —$(CHR')_q$— chain, K represents —CO—, —$SO_2$— or —$CH_2$—, L can be a carrier system, a reporter ligand, a solubility-mediating group or OH, M can, independently of L, be a carrier system, a reporter ligand, a solubility-mediating group or hydrogen, Q represents NH, O, S or NR", R' can be selected, independently of each other, from a group consisting of H, OH, SH, $NH_2$, NHR", $N_3$, alkyl (where alkyl can be methyl, ethyl, n-propyl, n-butyl, iso-butyl, tert-butyl or longer-chain, branched or unbranched, saturated or unsaturated alkyl chains), aryl (where aryl can be phenyl, 2-pyridyl or 4-pyridyl) or aralkyl (where aralkyl can be benzyl, naphthylmethyl or β-naphthylmethyl), R" represents protective groups such as, for example, Boc, Fmoc, Z, Pyoc, Alloc or other protective groups which are customary in peptide chemistry, or else represents alkyl substitution (where alkyl can be methyl, ethyl, n-propyl, n-butyl, iso-butyl, tert-butyl or longer-chain, branched or unbranched, saturated or unsaturated alkyl chains), aryl (where aryl can be phenyl, 2-pyridyl or 4-pyridyl) or aralkyl (where aralkyl can be benzyl, naphthylmethyl or β-naphthylmethyl), m can be 0, 1, 2 or 3, n can be 0, 1, 2, 3 or 4, p can be 0, 1 or 2, q can be 0, 1 or 2, and r can be 0 or 1, and s can assume values of between 1 and 30.

When r=1 in all the monomers, this structural component then occurs alternately and represents 50% of the total molecule. When r is 0 (zero) in individual monomers, the proportion of this structural component is correspondingly reduced to, for example, 40, 30 or 20%. This structural component should occur at least once in the total molecule.

Compounds of the general formula (I) are preferred in which

A represents —$(CH_2)_n$— or —CO—,

B represents all natural nucleotide bases, such as, for example, thymine, uracil, cytosine, adenine, guanine or hypoxanthine, or halogenated precursors thereof, which are optionally substituted on the amino groups by protective groups such as acetyl, trifluoroacetyl, trichloroacetyl, benzoyl, phenylacetyl, benzyloxycarbonyl, tert-butyloxycarbonyl, allyloxycarbonyl, (9-fluorenyl)methoxycarbonyl or other protective groups which are customary in peptide and nucleic acid chemistry, or which have a free amino group, D represents —$(CO)_p$—, E and G, independently of each other, represent —CHR—, where R represents H or a residue of a natural or unnatural amino acid, for example from glycine, alanine, valine, leucine, isoleucine, serine, threonine, cysteine, methionine, phenylalanine, tyrosine, histidine, tryptophane, lysine, ornithine, asparagine, aspartic acid, glutamine, glutamic acid, arginine, proline, hydroxypyroline, sarcosine, dehydroamino acids, such as, for example, dehydroalanine or dehydro-α-aminobutyric acid, or other unnatural amino acids, such as phenylglycine, 2-pyridylalanine, 3-pyridylalanine, 4-pyridylalanine, 1-naphthylalanine or 2-naphthylalanine, optionally having protective groups, in their D or L form, or, where appropriate, E and G are linked to each other by way of a —$(CHR')_q$— chain, K can be —CO—, —$SO_2$— or —$CH_2$—, L can be a carrier system, a reporter ligand, a solubility-mediating group or hydrogen, M can, independently of L, be a carrier system, a reporter ligand, a solubility-mediating group or hydrogen, Q represents NH, O or NR", R' can be selected, independently of each other, from a group consisting of H, OH, SH, $NH_2$, NHR", $N_3$, alkyl (where alkyl can be methyl, ethyl, n-propyl, n-butyl, iso-butyl, tert-butyl or longer-chain, branched or unbranched, saturated or unsaturated alkyl chains), aryl (where aryl can be phenyl, 2-pyridyl or 4-pyridyl) or aralkyl (where aralkyl can be benzyl, naphthylmethyl or β-naphthylmethyl), R" represents protective groups such as, for example, Boc, Fmoc, Z, Pyoc, Alloc or other protective groups which are customary in peptide chemistry, or else represents alkyl substitution (where alkyl can be methyl, ethyl, n-propyl, n-butyl, iso-butyl, tert-butyl or longer-chain, branched or unbranched, saturated or unsaturated alkyl chains), aryl (where aryl can be phenyl, 2-pyridyl or 4-pyridyl) or aralkyl (where aralkyl can be benzyl, naphthylmethyl or β-naphthylmethyl), m can be 0, 1, 2 or 3, n can be 0, 1, 2 or 3, p can be 0 or 1, q can be 0, 1 or 2, r can be 0 or 1, and s can assume values of between 3 and 20.

A carrier system or reporter ligand is intended to mean a cell-specific binding and recognition agent which binds specifically to the cell surface and which brings about internalization of the nucleic acid-binding oligomers on which the invention is based. The internalization can take place in different ways, for example by endocytosis or active transport mechanisms.

The cell surface can be constructed from a protein, polypeptide, carbohydrate, lipid or a combination thereof. Uptake into a cell is typically brought about by surface receptors. For this reason, the binding and recognition agent can be a natural or synthetic ligand of a receptor.

The ligand can be a protein, polypeptide, carbohydrate, lipid, steroid or a combination thereof, which is provided with functional groups which are so arranged that they can be recognized by the cell surface structure. The ligand can also be a component, or the entirety, of a biological organism, for example of a virus or a cell, or be an artificial transport system, for example liposomes. Furthermore, the ligand can be an antibody or an analogue of an antibody.

Different ligands must be employed for directing the oligomers to different cells.

Carbohydrates, such as, for example, mannose, polycations, such as, for example, polylysines, polyarginines or polyornithines, basic proteins, such as, for example, avidin, and also glycopeptides, steroids, peptides or lipopeptides are preferably used as ligands for directing the oligomers to macrophages (G. Y. Chu et al., WO 9304701).

Solubility-mediating groups are intended to mean functional groups which mediate solubility in water. These groups can be, for example, esters or amides of amino acids, hydroxycarboxylic acids, aminosulphonic acids, hydroxysulphonic acids or diamines. Amides of diaminocarboxylic acids, such as ornithine, lysine or 2,4-diaminobutyric acid, are preferred.

In the present application, nucleic acid-binding oligomers are described in which the great variability of the structural components from DE 4 331 012.5 has been combined with the properties of the aminoethylglycine structural components (WO 92/20703 and WO 93/12129, obtainable commercially from Millipore). The structural components which are employed for the oligomerization have been described in WO 92/20703 and WO 93/12129. Derivatives of the structural components which are described can be prepared by means of reaction steps which are known from the literature.

DESCRIPTION OF THE EXPERIMENTS

Investigations on the hybridization properties and also on stability towards nucleases and proteases were carried out in analogy with the experiments in DE 4 331 012.5. Capillary electrophoresis measurements were carried out as an additional investigative method for examining the hybridization properties.

General Section

Oligomerization

While the linking of the structural components to form oligomers can take place in solution, it is preferably carried out by means of solid phase synthesis (see: Merrifield, R. B., J. Am. Chem. Soc., 85, (1963), 2149). A peptide synthesizer, in particular the 431-A model from Applied Biosystems, is preferably employed for this purpose. Various commercially available resins are available for use as polymeric supports; the PAM, MBHA and HMP resins from Applied Biosystems are preferably used. The structural components are linked, in analogy with conventional peptide synthesis, by selective use of a protective group strategy at the N terminus, preferably employing the Fmoc method or the Boc method. Activation is as a rule effected in N-methyl-2-pyrrolidone (NMP) by reacting with hydroxybenzotriazole/ dicyclohexylcarbodiimide, or else using other known activation methods from peptide chemistry (for example uronium salts, such as TBTU, HBTU, BOP, PYBOP, etc., in NMP or other solvents, such as DMF, DMSO or DCM). Subsequent to the oligomerization, the solid phase-bound compounds are separated off using special cleavage reagents such as HF or trifluoromethanesulphonic acid (Boc method; PAM or MBHA resin), or using trifluoroacetic acid (Fmoc method; HMP resin), and removed from the polymeric support by filtration. Examples of well known reviews containing detailed descriptions of the method employed are a) Barany, G., Kneib-Cordonier, N., Mullen, D. G., Int. J. Pept. Protein Res., 30, 1987, 705ff and b) Fields, G. B., Noble, R. C., Int. J. Pept. Protein Res., 35, 1990, 161–214. The reaction products are isolated by preparative HPLC, in particular by means of the reversed phase method using RP 8 columns and employing a solvent mixture such as an ascending gradient of trifluoroacetic acid in acetonitrile or acetonitrile/water. The compounds are characterized by mass spectroscopy, in particular.

EXAMPLE 1

Solid phase Synthesis of $NH_2$—$T_1$—$T_2$—$T_1$—$T_2$—$T_1$—$T_2$—$T_1$—$T_2$—Lys—$NH_2$ $T_1$=Aminoethylglycine-thymine structural component, in accordance with WO 92/20703

$T_2$=L-trans-4-Amino-N-[(thymin-1-yl)-acetyl]-proline structural component, in accordance with DE 43 31 012.5

The oligomerization is effected using the programme, which exists in the ABI 431-A peptide synthesizer, for Boc small-scale reactions.

32.5 mg (0.025 mol) of MBHA resin are initially introduced into a reaction vessel. The support is neutralized with diisopropylethylamine and washed with DCM. The activation of 1 mmol of Boc-Lys(2-chloro-Z)-OH (0.41 g) and, at any one time, either 50 mg of the $T_2$ structural component or 48 mg of the $T_1$ structural component is effected by reacting them with 135 mg (1.0 mmol) of hydroxybenzotriazole and 206 mg (1.0 mmol) of dicyclohexylcarbodiimide in N-methyl-2-pyrrolidone (NMP). To improve the solubility of the structural components, the hydroxybenzotriazole is introduced, together with NMP, into the cartridge containing the amino acid. Prior to each coupling step, the tert-butyloxycarbonyl protective group of the support-bound intermediate is cleaved off by treating with trifluoroacetic acid, and the support is then neutralized with diisopropylethylamine and washed with DCM. Stepwise coupling to the polymeric support then follows. After the final coupling, the Boc protective group is removed by treating with trifluoroacetic acid. Weighing the dried support indicates an increase in weight of 56.1 mg. The oligomer is cleaved off the support by treating the polymer for 2 hours with 4.5 ml of HF and 0.5 ml of anisole at 0° C. in a Teflon flask. After effecting the HF-mediated cleavage, the residue is stirred 4 times with 15 ml of absolute diethyl ether on each occasion in order to dissolve out adhering anisole. The ether is carefully separated off after 15 minutes in each case. The oligomer is now extracted with 60 ml of 30% acetic acid (4×15 ml, for 15 minutes in each case), and the solution is separated off from the polymer by filtering through a D3 frit, and the filtrate is lyophilized.

46.5 mg of crude product are obtained, which crude product is purified by RP-HPLC. A Eurosil Bioselect 300 A (5 μm) column is used as the stationary separation medium while employing the following elution system:

Eluent A: 0.1% TFA in water,

Eluent B: 0.1% TFA in water/acetonitrile (3/7)

The gradient is designed as follows:

| Gradient (min) | Eluent A (%) | Eluent B (%) |
| --- | --- | --- |
| 0.00 | 95 | 05 |
| 60.00 | 40 | 60 |
| 40.00 | 20 | 80 |
| 45.00 | 20 | 80 |
| 50.00 | 95 | 05 |

Detection is at 260 nm using a UV detector. The oligomers in Examples 2 to 7 were purified in an analogous manner to that used in Example 1. The retention time of the target substance is 15.2 minutes.

Following the HPLC, the purified oligomer is lyophilized. A yield of highly pure product of 35.7 mg (0.0153 mmol, 61.2% based on the theoretically possible quantity; 63.6% based on the actual quantity bound to the resin) is obtained. The oligomer is characterized by mass spectroscopy (LDI method). The theoretical molecular weight is 2323 g/mol, with 2324.0 g/mol being measured.

EXAMPLE 2

Solid Phase Synthesis of $NH_2$—$T_1$—$T_3$—$T_1$—$T_3$—$T_1$—$T_3$—$T_1$—$T_3$—Lys—$NH_2$ $T_1$=Aminoethylglycine-thymine structural component, in accordance with WO 92/20703

$T_3$=L-cis-4-Amino-N-[(thymin-1-yl)-acetyl]-proline structural component, in accordance with DE 43 31 012.5

The oligomerization was carried out in an analogous manner to that in Example 1. 70.0 mg of crude product are obtained, which crude product is purified by RP-HPLC.

The retention time of the target substance is 16.3 minutes.

Following the HPLC, the purified oligomer is lyophilized. A yield of highly pure product of 20.4 mg (0.0087 mmol, 34.9% based on the theoretically possible quantity; 36.8% based on the actual quantity bound to the resin) is obtained. The oligomer is characterized by mass spectroscopy (LDI method). The theoretical molecular weight is 2323.3 g/mol, with 2325.6 g/mol being measured.

EXAMPLE 3

Solid Phase Synthesis of $NH_2$—($T_1$—$T_2$—$T_2$—$T_2$)$_3$—Lys—$NH_2$ SEQ ID NO: 1

$T_1$=Aminoethylglycine-thymine structural component, in accordance with WO 92/20703

$T_2$=L-trans-4-Amino-N-[(thymin-1-yl)-acetyl]proline, in accordance with DE 43 31 012.5

The oligomerization was carried out in an analogous manner to that in Example 1.

65.2 mg of crude product are obtained, which crude product is purified by RP-HPLC.

The retention time of the target substance is 20.5 minutes. Following the HPLC, the purified oligomer is lyophilized. A yield of highly pure product of 15.9 mg (0.0046 mmol; 18.4% based on the theoretically possible quantity; 21.0% based on the actual quantity bound to the resin) is obtained. The oligomer is characterized by mass spectroscopy (LDI method, measurement carried out without adding any mass standard). The theoretical molecular weight is 3448.3 g/mol, with 3449 g/mol being measured.

EXAMPLE 4

Solid phase synthesis of $NH_2$—$(T_1$—$T_2$—$T_2)_4$—Lys—$NH_2$ SEQ ID NO: 2

$T_1$=Aminoethylglycine-thymine structural component, in accordance with WO 92/20703

$T_2$=L-trans-4-Amino-N-[(thymin-1-yl)-acetyl]proline, in accordance with DE 43 31 012.5

The oligomerization was carried out in an analogous manner to that in Example 1.

60.2 mg of crude product are obtained, which crude product is purified by RP-HPLC.

The retention time of the target substance is 19.6 minutes. Following the HPLC, the purified oligomer is lyophilized. A yield of highly pure product of 11.8 mg (0.0034 mmol; 13.7% based on the theoretically possible quantity; 15.7% based on the actual quantity bound to the resin) is obtained. The oligomer is characterized by mass spectroscopy (LDI method, no internal mass standard is added). The theoretical molecular weight is 3436.3 g/mol, with 3442 g/mol being measured.

EXAMPLE 5

Solid Phase Synthesis of $NH_2$—$(T_2$—$T_1)_4$—Lys—$NH_2$ $T_1$=Aminoethylglycine-thymine structural component, in accordance with WO 92/20703

$T_2$=L-trans-4-Amino-N-[(thymin-1-yl)-acetyl]proline, in accordance with DE 43 31 012.5

The oligomerization was carried out in an analogous manner to that in Example 1.

59.3 mg of crude product are obtained, which crude product is purified by RP-HPLC.

The retention time of the target substance is 17.4 minutes. Following the HPLC, the purified oligomer is lyophilized. A yield of highly pure product of 44.5 mg (0.0192 mmol; 76.6% based on the theoretically possible quantity; 66.0% based on the actual quantity bound to the resin) is obtained. The oligomer is characterized by mass spectroscopy (LDI method, no internal mass standard is added). The theoretical molecular weight is 2323.2 g/mol, with 2325 g/mol being measured.

EXAMPLE 6

Solid Phase Synthesis of $NH_2$—$(T_1$—$T_4)_6$—Lys—$NH_2$ SEQ ID NO: 3

$T_1$=Aminoethylglycine-thymine structural component, in accordance with WO 92/20703

$T_4$=D-trans-4-Amino-N-[(thymin-1-yl)-acetyl]proline, in accordance with DE 43 31 012.5

The oligomerization was carried out in an analogous manner to that in Example 1.

89 mg of crude product are obtained, which crude product is purified by RP-HPLC.

The retention time of the target substance is 23.0 minutes. Following the HPLC, the purified oligomer is lyophilized. A yield of highly pure product of 78 mg (0.022 mmol; 91% based on the theoretically possible quantity; 90% based on the actual quantity bound to the resin) is obtained. The oligomer is characterized by mass spectroscopy (LDI method, no internal mass standard is added). The theoretical molecular weight is 3412.3 g/mol, with 3417 g/mol being measured.

EXAMPLE 7

Solid Phase Synthesis of $NH_2$—$(T_1$—$T_4$—$T_4)_4$—Lys—$NH_2$ SEQ ID NO: 4

$T_1$=Aminoethylglycine-thymine structural component, in accordance with WO 92/20703

$T_4$=D-trans-4-Amino-N-[(thymin-1-yl)-acetyl]proline, in accordance with DE 43 31 012.5

The oligomerization was carried out in an analogous manner to that in Example 1.

81.0 mg of crude product are obtained, which crude product is purified by RP-HPLC.

The retention time of the target substance is 22.0 minutes. Following the HPLC, the purified oligomer is lyophilized. A yield of highly pure product of 70.7 mg (0.02 mmol; 81.5% based on the theoretically possible quantity; 63.1% based on the actual quantity bound to the resin) is obtained. The oligomer is characterized by mass spectroscopy (LDI method, no internal mass standard is added). The theoretical molecular weight is 3436.3 g/mol, with 3462 g/mol being measured.

EXAMPLE 8

Solid Phase Synthesis of $NH_2$—$(T_1$—$T_4$—$T_2)_4$—Lys—$NH_2$ SEQ ID NO: 5

$T_1$=Aminoethylglycine-thymine structural component, in accordance with WO 92/20703

$T_2$=L-trans-4-Amino-N-[(thymin-1-yl)-acetyl]proline, in accordance with DE 43 31 012.5

$T_4$=D-trans-4-Amino-N-[(thymin-1-yl)-acetyl]proline, in accordance with DE 43 31 012.5

The oligomerization was carried out in an analogous manner to that in Example 1.

59.0 mg of crude product are obtained, which crude product is purified by RP-HPLC.

The retention time of the target substance is 20.0 minutes. Following the HPLC, the purified oligomer is lyophilized. A yield of highly pure product of 52.2 mg (0.015 mmol; 60.8% based on the theoretically possible quantity; 61.3% based on the actual quantity bound to the resin) is obtained. The oligomer is characterized by mass spectroscopy (LDI method). The theoretical molecular weight is 3436.3 g/mol, with 3440 g/mol being measured.

Test For Biological Stability Towards Proteases and Nucleases

EXAMPLE 9

Stability Towards Proteinase K

In each case, 20 μl of 1M Tris/HCl (pH 7.5), 80 μl of a 50 mM solution of calcium chloride, and 1 U of proteinase K (Serva) were added to 75 μg each of the compounds from Example 1 and Example 2, each of which was in 75 μl of double distilled water, and the mixtures were incubated at 37° C. for 3 hours. Each of the reaction mixtures was then investigated by HPLC (reversed phase, Eurosil-Bioselect, eluent: 5–70% 0.1% trifluoroacetic acid in water/acetonitrile (3⁄7) against 0.1% trifluoroacetic acid in water). In neither case was it possible to detect any newly formed degradation product, whereas the signals of the compounds from Example 1 and Example 2 were present as before. Consequently, the compounds are stable towards proteinase K.

EXAMPLE 10

Stability Towards S1 Nuclease

In each case, 20 μl of nuclease buffer (Promega) and 4 μl of S1 nuclease (Promega, 50 U/ml) were added to 75 μg each of the compounds from Example 1 and Example 2, each of which was in 75 μl of double distilled water, and the mixtures were incubated at 37° C. for 3 hours. Each of the reaction mixtures was then investigated by HPLC (reversed phase, Eurosil-Bioselect, eluent: 5–70% 0.1% trifluoroacetic acid in water/acetonitrile (3⁄7) against 0.1% trifluoroacetic acid in water). In neither case was it possible to detect a newly formed degradation product, whereas the signals of the compounds from Example 1 and Example 2 were present as before. Consequently, the compounds are stable towards S1 nuclease.

EXAMPLE 11

Determination of the Temperature at Which Selected Oligomers Anneal to an $A_8$ DNA Strand or an $A_{12}$ DNA Strand.

The corresponding DNA strands were prepared on an "ABI 380B" Applied Biosystems DNA synthesizer using the phosphoramidite method in accordance with the manufacturer's (Applied Biosystems) small-scale cycle.

The annealing temperature was determined using a Perkin Elmer "Lambda Bio" UV-Vis spectrometer and employing the "PE-TEMP" method specified by the manufacturer.

For this purpose, sufficient PNA is dissolved in 700 μl of water to give an absorbtion of 0.3. The same is done with the corresponding DNA strand. The two strands are then combined and the volume of water is increased to 1.5 ml. The combined strands are next heated at 95° C. for 5 minutes and then cooled slowly overnight in a Styropor vessel.

The absorbtion of the double strands in the temperature range of from 20° C. to 80° C. is then investigated using the "PE-temp" method. The turning point (maximum of the 1st derivative) of the resulting absorption curve then corresponds to the annealing temperature which is measured on the temperature scale.

The following oligomers were measured:

| Oligomers from Example | DNA strand | Annealing temp. in ° C. |
| --- | --- | --- |
| 1 | $A_8$ | 47.0 |
| 2 | $A_8$ | 27.0 |
| 3 | $A_{12}$ | 34.4 |
| 4 | $A_{12}$ | 48.8 |

-continued

| Oligomers from Example | DNA strand | Annealing temp. in ° C. |
| --- | --- | --- |
| 5 | $A_8$ | 46.0 |
| 6 | $A_{12}$ | 27.0 | the oligomer $A_{12}$ is designated SEQ ID NO:6.

EXAMPLE 12

Demonstration of Strand Displacement by Nucleic Acid-Binding Oligomers in Double-Stranded Plasmid DNA In that which follows, the test is described for experimentally demonstrating DNA double strand displacement by the nucleic acid-binding oligomers. This ability to displace DNA double strands cannot be achieved using a ribose phosphate backbone, a ribose methylphosphonate backbone, a ribose phosphorothioate backbone, or other nucleic acid-like backbone types.

The plasmid DNA employed in the example is a model substrate for demonstrating DNA double strand displacement. Other plasmids which contain appropriate target sequences having a base sequence which is complementary to the nucleic acid-binding oligomers to be tested can also be used for the test in the same way.

In the test described here, use is made of double-stranded, circular plasmid DNA which is 4880 base pairs in length and which contains, 1150 base pairs apart, two regions of polyadenine sequence containing at least nine consecutive adenine nucleotides.

Seven samples, which were set up in parallel and which were designated (1–7), each contained 1.0 μg of uncut plasmid DNA in 14 μl of $H_2O$. 1 μl of solution containing 0.0001 μg, 0.001 μg, 0.01 μg, 0.1 μg and 1.0 μg, respectively, of nucleic acid-binding oligomer from one of Examples 1 to 5 was added to samples 3 to 7, respectively, and the mixtures were incubated in sealed Eppendorf tubes at 37° C. for 45 min. 4 μl of buffer (250 mM Na acetate, 1M NaCl, 2.5% glycerol, 5 mM $ZnCl_2$, pH 4.4) were then added to all the samples while 1 μl of *Aspergillus oryzae* S1 nuclease (from Boehringer Mannheim), having an activity of 10 U/μl, was also added to each of samples 2 to 7. After these samples had been incubated at 30° C. for 15 minutes, they were placed on ice and 1 μl of 0.5M EDTA and 3 μl of loading buffer (50% glycerol, 0.25% bromophenol blue in 40 mM Tris-HCl, 20 mM sodium acetate, 1 mM EDTA, pH 7.2) were added; the samples were then immediately subjected to electrophoretic separation on 1.2% agarose gels and, after staining with ethidium bromide, the sizes of the resulting plasmid fragments in the gel were determined on a UV light transilluminator at 254 nm by comparing with a molecular weight standard (1 kb ladder, from Gibco-BRL, D-7514 Eggenstein).

It was found that, in the samples (samples 5–7) containing a concentration of the oligomer from Example 1>0.001 μg (≈4.3.10⁻⁷M), the S1 nuclease reaction produced DNA fragments of 4880 base pairs (plasmid linearization) and of 3270, 2570 and 1150 base pairs. These fragments demonstrate that the octamer from Example 1 bound in a sequence-selective manner to the double-stranded DNA leading to strand displacement and subsequent cleavage by S1 nuclease.

DNA fragments of 3730, 4480, 2570 and 1150 base pairs in length, which confirm the sequence-selective double strand displacement, were likewise detected in samples 5–7 using a modified test mixture in which a plasmid DNA which had been linearized by restriction endonuclease digestion in the immediate vicinity of one of the two regions of polyadenine sequence was added to the samples in place of the circular, uncut plasmid DNA.

Furthermore, DNA double strand displacement was also detected in the double-stranded plasmid DNA when the octamer from Example 1 was employed at higher salt concentrations, using 5 mM Tris HCl, 1 mM Mg Cl$_2$, 10 mM NaCl, pH 7.0, in place of water.

In addition, a comparable DNA double strand displacement was demonstrated in this test using the oligomers from Examples 3 to 5 by way of example. The oligomers from Examples 3 to 5 also gave rise in the test, at 0.01 μg to 0.001 μg (approximately $5·10^{-6}M$ to $5·10^{-7}M$), to a sequence-selective cleavage of double-stranded DNA by *Aspergillus oryzae* S1 nuclease.

This series of tests rendered it possible to demonstrate the concentration-dependent and sequence-selective binding of the oligomers from Examples 1 to 5 to double-stranded DNA and to demonstrate the presence of the single-stranded DNA, which arose as a result, by means of digestion with S1 nuclease (at high salt concentrations to ensure the single-strand specificity of the S1 nuclease).

EXAMPLE 13

Gel Shift Analyses

Gel shift analyses can verify, qualitatively and quantitatively, the potential ability of nucleic acid-binding oligomers to hybridize to normal diester oligomers. For this purpose, single-stranded DNA of appropriate base sequence is incubated with the oligomer to be investigated and the mixture is then fractionated by gel electrophoresis. As compared with free DNA, hybridized DNA exhibits a clear shift in the gel. By varying the concentration of the nucleic acid-binding oligomers, it becomes possible to make quantitative statements about the extent of the hybridization.

Implementation of the Test

1 μg of diester oligonucleotide of appropriate base sequence is labelled at the 5' end, in the current manner and in a volume of 10 μl, using polynucleotide kinase and γ-ATP (Sambrook, Fritsch, Maniatis: Molecular Cloning, A Laboratory Manual, Cold Spring Harbor, 1989). After the labelling, the sample is heated at 70° C. for 10 min to denature the enzyme and is then mixed with 9 μg of unlabelled oligomer. 1 μl of this mixture is then treated with a desired quantity of the nucleic acid-binding oligomer to be tested (1–10 μg) and the whole is incubated (hybridization) in a volume of 20 μl at 22° C. (room temperature) for 30 min. After that, the sample is placed on ice for 30 min. An unhybridized, labelled oligomer is treated in the same way and serves as the control. The samples are loaded onto a 15% polyacrylamide gel in 1×Tris-borate-EDTA buffer. The gel and the buffer have been precooled in a refrigerator (8° C.), and the electrophoresis is left to run overnight at 55 V in a refrigerator. Following the electrophoresis, an autoradiogram is prepared on AGFA film (exposure times 1 to 16 hours).

Results

The compounds from Examples 1, 3, 4 and 6 already exhibit clear gel shifts when they are present at a concentration which is equimolar to that of a diester, and these shifts are complete when the compounds are present in a 5 to 10-fold excess; this verifies the very good hybridization properties of these compounds. In comparison, the compounds from Examples 5 and 7 exhibit a somewhat lower hybridization potential.

Legend to FIG. 1

Agarose gel electrophoresis of the test samples from Example 5 for the purpose of demonstrating DNA double strand displacement following incubation of plasmid DNA with the DNA-binding octamer from Example 1 and subsequent reaction with S1 nuclease. The contents of the tracks of the ethidium bromide-stained gel are as follows:

0=molecular weight standard for double-stranded fragments of DNA

1=uncut plasmid DNA (identical substrate for each test sample)

2=as 1, but containing 10 U of S1 nuclease

3–7=as 2, but additionally containing 0.0001; 0.001, 0.01; 0.1 and 1.0 μg of DNA-binding octamer from Example 1

DNA double strand displacement can be detected in the test when the concentration of the octamer from Example 1 is $>4.3\times10^{-7}M$.

EXAMPLE 14

Capillary Electrophoresis

Introduction

The hybridization properties of oligonucleotide analogues are frequently conveyed by way of the melting temperature, $T_M$, of the complementary oligonucleotides. Very recently, capillary gel electrophoresis (CE using a solid gel in the capillary) has also been employed for determining PNA-DNA binding (Rose, D. J. Anal. Chem. (1993), 65, 3545–3549). Dynamic liquid gels have also been successfully employed for separating DNA fragments (Barron, A. E.; Soane, D. S. & Blanch, H. W. J. Chromatogr. (1993), 652, 3–16).

Dynamic gel capillary electrophoresis (DGCE) is particularly suitable for separating oligomeric DNA nucleotides due to its high degree of reproducibility and its availability.

Experimental

Capillary Electrophoresis (CE)

The investigations were carried out on an ABI 270A-HT (Applied Biosystems, Weiterstadt); any other CE apparatus having a UV detector is also suitable. The conditions are given in Table 1. The data were transferred to a PC via an AD converter and recorded and evaluated using the HPCHEM software (Hewlett-Packard, Waldbronn).

Hybridization

The nucleic acid-binding octamer from Example 1, at a constant concentration of 45 μM in Tris-HCl (5 mM, 0.1 ml), was hybridized, in differing ratios, to the complementary DNA octamer δ(A)$_8$. The ratios of $^{0.2}/_1$, $^{0.25}/_1$, $^{0.33}/_1$, $^{0.5}/_1$, $^{1}/_1$, $^{2}/_1$ and $^{3}/_1$ were chosen.

The samples were heated in parallel, and in accordance with the standardized method, at 93° C. for 5 min and were then gradually cooled down to RT; the samples were then measured directly after they had been diluted 1:5 with water.

TABLE 1

Measurement parameters for determining hybridization using DGCE

| | | |
|---|---|---|
| Buffer | 100 nM Tris/borate + 0.5% dextran, pH 8.5 | |
| Capillary: | Fused silica (ABI) | |
| | Lengths: total: | 50 cm effective: 29 cm |
| | Internal diameter: | 50 μm |

TABLE 1-continued

Measurement parameters for determining hybridization using DGCE

| | | |
|---|---|---|
| Measurement parameters: | Vacuum injection: | $1.7 \cdot 10^4$ Pa |
| | Injection time: | 3 sec |
| | Voltage: | 25 kV |
| | Temperature: | 30° C. |
| | Run time: | 10 min |
| Detection: | | 257 nm |
| Column conditioning: | Washing vacuum: | $6.8 \cdot 10^4$ Pa |
| | 1st washing step: | 2 min, 0.1 N NaOH |
| | 2nd washing step: | 6 min, buffer |

Results and Discussion

Figure 2:
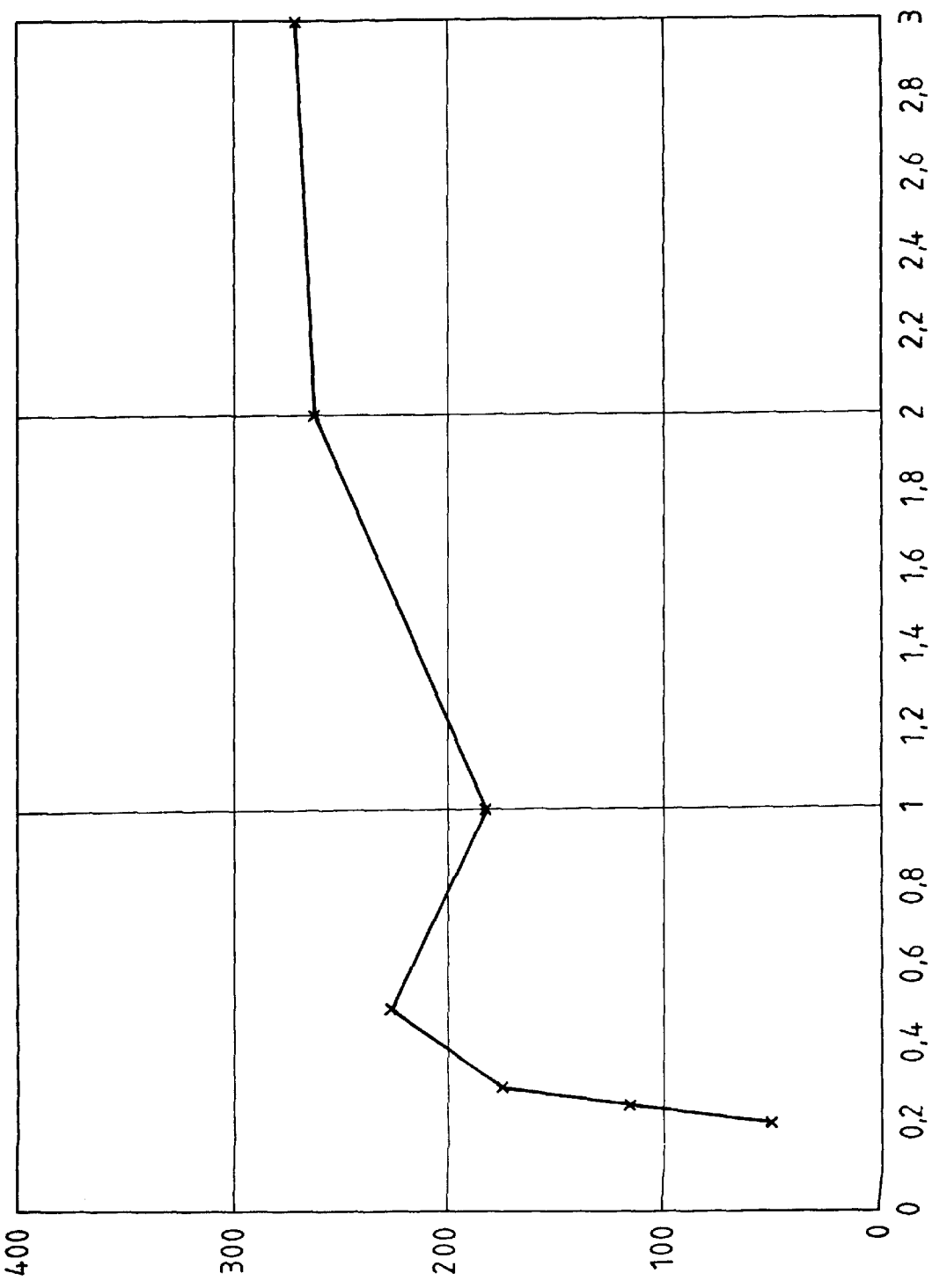

The hybridization yield plotted against the concentration of complementary DNA octamer $\delta(A)_8$ shows that the hybridization yield increases strongly up to a ratio of 1:0.5. After that, the quantity of hybridization product remains relatively constant despite increasing concentration of complementary $\delta(A)_8$ octamer (FIG. 2). The ratio of 1:0.5 indicates that the nucleic acid-binding octamer from Example 1 hybridizes to the complementary $\delta(A)_8$ octamer in a ratio of 2:1.

Legend to FIG. 2

In the figure, the maximum peak height of the hybridization product formed from the nucleic acid-binding octamer from Example 1 and the complementary $\delta(A)_8$ octamer (y axis) is plotted against the relative concentration of complementary $\delta(A)_8$ octamer (x axis). Maximum hybridization is achieved at a 2:1 ratio of nucleic acid-binding octamer from Example 1 to complementary $\delta(A)_s$ octamer.

We claim:

1. A compound of the formula:

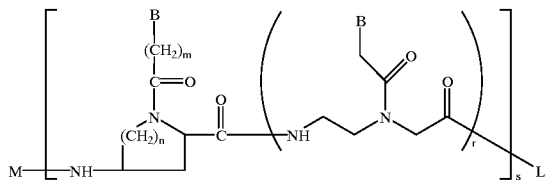

wherein
- L represents a carrier system, a reporter ligand, a solubility-mediating group or hydrogen,
- B represents a nucleotide base selected from the group consisting of thymine, uracil, cytosine, adenine, guanine or hypoxanthine, or derivatives thereof, or halogenated precursors thereof, which are optionally substituted on the amino groups by protective groups which are customary in peptide and nucleic acid chemistry, or which have free amino groups,
- m represents 0, 1, 2 or 3,
- n represents 0, 1, 2 or 3,
- M can, independently of L, be a carrier system, a reporter ligand, a solubility-mediating group or hydrogen,
- r represents 0 or 1, and
- s represents a value between 1 and 30, with the proviso that the structure:

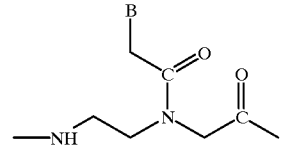

occurs at least once in the compound.

2. Compound of claim 1, wherein
- B represents thymine,
- L represents —$NH_2$,
- M represents —Lys—$NH_2$,
- m equals 1,
- n equals 1, and
- s equals 4.

3. Compound of claim 1, wherein the protective group is selected from the group consisting of acetyl, trifluoroacetyl, trichloroacetyl, benzoyl, phenylacetyl, benzyloxycarbonyl, tert-butyloxycarbonyl, allyloxycarbonyl, and (9-fluorenyl) methoxycarbonyl.

* * * * *